US009682902B2

(12) United States Patent
Partridge et al.

(10) Patent No.: US 9,682,902 B2
(45) Date of Patent: Jun. 20, 2017

(54) MEMBRANE SEPARATION PROCESS USING MIXED VAPOR-LIQUID FEED

(71) Applicants: Randall D. Partridge, Califon, NJ (US); Robert P. Lucchesi, Flemington, NJ (US); George P. Walchuk, Flemington, NJ (US); David T. Ferrughelli, Flemington, NJ (US); George L. Kellogg, Hector, NY (US); Richard Bergman, Horseheads, NY (US); Kenneth Joseph Drury, Big Flats, NY (US)

(72) Inventors: Randall D. Partridge, Califon, NJ (US); Robert P. Lucchesi, Flemington, NJ (US); George P. Walchuk, Flemington, NJ (US); David T. Ferrughelli, Flemington, NJ (US); George L. Kellogg, Hector, NY (US); Richard Bergman, Horseheads, NY (US); Kenneth Joseph Drury, Big Flats, NY (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 483 days.

(21) Appl. No.: 14/077,375

(22) Filed: Nov. 12, 2013

(65) Prior Publication Data
US 2014/0142363 A1 May 22, 2014

Related U.S. Application Data

(60) Provisional application No. 61/727,329, filed on Nov. 16, 2012.

(51) Int. Cl.
*C10G 31/11* (2006.01)
*C07C 7/00* (2006.01)
(Continued)

(52) U.S. Cl.
CPC .......... *C07C 7/005* (2013.01); *B01D 61/362* (2013.01); *B01D 61/366* (2013.01); *B01D 63/00* (2013.01);
(Continued)

(58) Field of Classification Search
None
See application file for complete search history.

(56) References Cited

U.S. PATENT DOCUMENTS 5,609,734 A * 3/1997 Streicher ................. C07C 7/005
203/39
5,670,052 A 9/1997 Ho et al.
(Continued)

FOREIGN PATENT DOCUMENTS

DE 4410243 C1 6/1995
WO 2008039762 A2 4/2008

OTHER PUBLICATIONS

The International Search Report and Written Opinion of PCT/US2013/069565 dated Mar. 13, 2014.

*Primary Examiner* — Tam M Nguyen
(74) *Attorney, Agent, or Firm* — David M. Weisberg; Jamie L. Sullivan; Amanda K. Jenkins

(57) ABSTRACT

The present invention pertains to a pervaporation membrane process for the separation of high octane fuel components from a gasoline feed stream comprising feeding a mixed phase vapor-liquid feed to a cyclone separation means to separate the liquid from the vapor, then sending the saturated vapor to the membrane, thereby extending the useful life of the membrane.

9 Claims, 7 Drawing Sheets

(51) Int. Cl.
  *B01D 61/36* (2006.01)
  *B01D 63/00* (2006.01)
  *F02D 19/06* (2006.01)
  *C10G 3/00* (2006.01)

(52) U.S. Cl.
  CPC ............... *C10G 3/00* (2013.01); *C10G 31/11* (2013.01); *F02D 19/0671* (2013.01); *B01D 2311/2676* (2013.01); *B01D 2313/90* (2013.01); *C10G 2300/305* (2013.01); *F02D 19/0649* (2013.01); *Y02P 30/20* (2015.11); *Y02T 10/36* (2013.01)

(56) References Cited

U.S. PATENT DOCUMENTS

| | | | |
|---|---|---|---|
| 7,582,143 B2 | 9/2009 | Berger et al. | |
| 7,803,275 B2 | 9/2010 | Partridge et al. | |
| 8,051,828 B2 | 11/2011 | Sengupta et al. | |
| 8,119,006 B2 | 2/2012 | Patil et al. | |
| 2002/0195251 A1 | 12/2002 | Underdown et al. | |
| 2004/0222157 A1* | 11/2004 | Minhas | B01D 61/02 210/651 |
| 2008/0011680 A1* | 1/2008 | Partridge | B01D 61/362 210/640 |
| 2009/0165759 A1 | 7/2009 | Sengupta et al. | |
| 2009/0247805 A1 | 10/2009 | Bournay et al. | |
| 2010/0155300 A1* | 6/2010 | Sabottke | C10G 35/04 208/134 |
| 2012/0270958 A1 | 10/2012 | Shaffer et al. | |

* cited by examiner

MEMBRANE SEPARATION PROCESS USING MIXED VAPOR-LIQUID FEED

CROSS-REFERENCE TO RELATED APPLICATIONS

This application claims the benefit of U.S. Provisional Application Ser. No. 61/727,329, filed on Nov. 16, 2012; which is incorporated herein in its entirety by reference.

BACKGROUND OF THE INVENTION

The present invention is directed to an improved lifetime membrane system for separating a gasoline feed stream using a pervaporation membrane. Such a system has potential for application to an "on-board" separation system for multiple fuel feed as illustrated in U.S. Pat. No. 7,803,275, for example.

Pervaporation is a well-known membrane process. Pervaporation has been and is being considered for low energy consumption separation of aromatics from streams. A multicomponent liquid feed may be separated based on a selective solution-diffusion mechanism, with the permeate removed as a vapor, retentate typically remaining a liquid.

Gasoline is a complex mixture of aliphatic and aromatic hydrocarbons, often with oxygenates such as ethanol, having a wide boiling range. Aromatics and oxygenates such as ethanol may be separated from a gasoline feed by pervaporation to obtain a higher-octane fuel. However, the wide boiling range, variable composition and volatility of market gasolines make separation with simple pervaporation membrane systems difficult and inefficient. Maintaining sufficient membrane flux and selectivity is a challenge. Conventional gasoline typically contains additives, and other high boiling constituents, that may benefit its use in conventional internal combustion engines, but have deleterious effects on sustained membrane performance.

Other separation systems have used complex systems including pre-fractionation, multi-stage membrane processing, and/or recycle with post-fractionation, to address these issues, but are generally not desirable for efficient or commercially cost effective membrane systems.

The present invention enables considerable simplifications to the pervaporation process, when separating wide boiling range feeds such as gasoline having conventional additives, for example. These simplifications can lead to the reduced cost and system complexity, while increasing the longevity of the pervaporation membrane to enable commercialization of this application.

SUMMARY OF THE INVENTION

The present invention relates to a method and apparatus for increasing the lifetime and efficiency of pervaporation membranes used for gasoline separations, or similar wide boiling hydrocarbon feeds such as naphtha for example. The gasoline feed is partially vaporized at a specified temperature and pressure and then separated into a saturated vapor fraction and a higher boiling liquid fraction by means of a flash drum separator, cyclone separator, or other suitable means. The saturated vapor fraction contacts the membrane, while the liquid fraction containing potential fouling components is bypassed to avoid contact with the primary pervaporation membrane, thereby extending the separation system's lifetime.

An embodiment of this invention uses a cyclone separator to substantially separate the fuel into vapor and liquid components, directing the saturated gasoline vapor to a plurality of selected channels of a monolithic membrane structure, while directing the remaining liquid fraction to effectively bypass the primary pervaporation membrane. The bypassed liquid fraction is combined with the retentate obtained on processing of the saturated vapor fraction through the pervaporation membrane.

When used as an on board gasoline separation system, the perimeter of the primary pervaporation membranes produce a HiRON fuel, while the bypass and retentate form the primary membrane produce a LoRON fuel.

DETAILED DESCRIPTION OF THE PREFERRED EMBODIMENTS

Separations of aromatics from gasoline, or similar wide-boiling mixtures, such as petroleum naphtha, can be improved by means of a separation of liquid and saturated vapor in a pervaporation membrane process employing a mixed phase vapor-liquid feed. Sustained higher permeate yields of aromatics can be a made possible in near adiabatic operations. Sustained longer membrane flux and simplified system configurations can be enabled with the present invention.

Partial vaporization of conventional fuels, such as gasoline, concentrates higher boiling point constituents in the liquid fraction of the feed. Their higher boiling components can contain feed additives and other constituents that are shown to be deleterious to the sustained flux of the pervaporation membrane. In the present invention, a separation stage comprising a separation means such as a cyclone that can substantially separate the saturated vapor from the liquid. The saturated vapor can be directed to a first pervaporation membrane system, and the liquid can be directed to a second system to accommodate the deleterious content, thereby improving the sustained flux and performance of the primary pervaporation membrane system when compared to processing the full feed.

Furthermore, adiabatic operation of the pervaporation membrane separation process can be improved by employing mixed phase vapor-liquid feed to the membrane. Progressive condensation of the vapor phase can provide heat to the membrane thereby minimizing the temperature change of the membrane resulting from the endothermic pervaporation process. Significant permeate yield gains can be made possible from near adiabatic operation using mixed-phase feed. Consequently, the membrane area required can be reduced. Mixed-phase vapor/liquid feed can enable considerable simplifications to the process scheme, i.e., pre-distillation of lower boiling components in the feed can be avoided, along with the associated pumps and controls. Use of inter-stage and/or internal heat exchangers to maintain pervaporation temperature can be reduced or eliminated.

The improved longevity membrane system may be used to produce a HiRON and LoRON fuel, where HiRON or high octane is defined as a fuel having a Research Octane Number above about 97, e.g., above about 100, and LoRON or low octane means a Research Octane Number below about 95. It may be employed as an "on-board" system, used to separate conventional gasoline into a low and high octane fuel to tailor engine fuel feed to engine operating needs, thereby substantially enhancing fuel economy, engine emissions, and engine performance.

Figure 1:
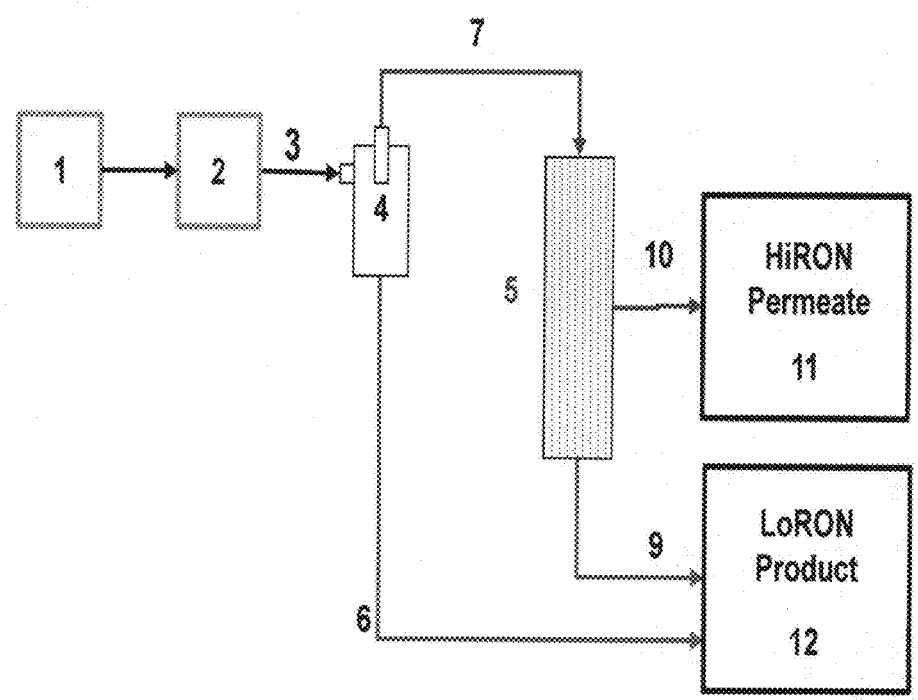
FIG. 1 diagrammatically illustrates a simple embodiment of the present invention.
Figure 2:
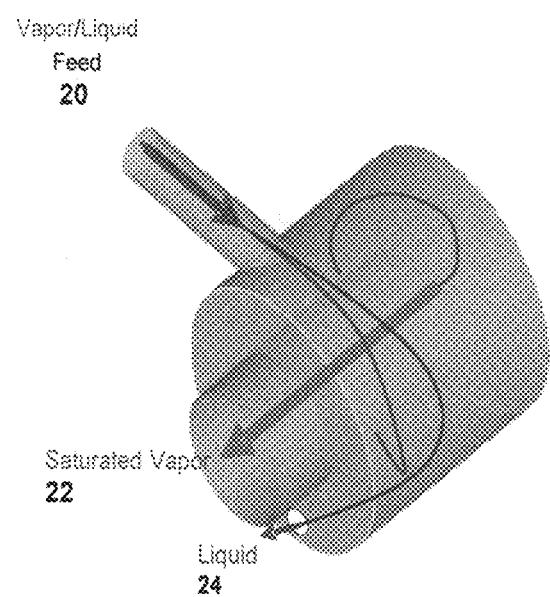
FIG. 2 shows a schematic of the separation apparatus used for improved lifetime membrane separation using mixed vapor-liquid feed.

Referring to FIG. 1, there is shown a very simplified schematic illustration of the improved lifetime membrane separation system of the present invention. A feed reservoir (1) can contain the wide boiling range material intended for membrane separation, such as conventional gasoline or naphtha, for example. The term "wide boiling range" in the context of gasoline or naphtha means a boiling range of greater than about 50° C., for example greater than about 150° C., from the initial boiling point to the final boiling point, as determined by ASTM Method D86-05. Gasoline boiling ranges from about 30° C. to about 200° C. can be typical based on this method. Aromatic constituents can be found in fractions boiling above about 80° C. Heater means (2) can be used to controllably heat the feed material to a partial vapor phase, whereby the feed (3) at the inlet to separation means (4) can be saturated vapor and liquid. Optional pump means (not shown) may be used to pressurize the feed to the heater (2) to help maintain the separator feed (3) in a combination of liquid and vapor phase amounts by controlling the temperature and pressure of the feed (3). The desired feed rate may be optionally controlled by a flow control valve (not shown). The desired feed pressure may alternatively be controlled by back pressure regulating means (8) operating on the retentate (9). In a preferred embodiment, the feed pressure $P_f$ and feed temperature $T_f$ can be controlled to provide an optimal saturated vapor and liquid mixture ratio to the separator (5). By optimal, in this context, we mean a vapor liquid mixture whereby sufficient high octane aromatic and oxygenate components in the feed can be maintained in the saturated vapor portion contacting the pervaporation membrane, and higher boiling point feed components and additives can be concentrated in the separated liquid stream (6). In one embodiment, the feed (3) can be about 90% saturated vapor, about 10% liquid, and separations means (4) can comprise a cyclone as illustrated in FIG. 2, operable to separate the feed liquid phase (6) from the feed saturated vapor phase (7). As illustrated in FIG. 2, the mixed vapor/liquid feed (20) can be substantially separated into two streams, a saturated vapor stream (22) and a liquid stream (24).

Referring back to FIG. 1, the saturated vapor stream (7) can be directed to a pervaporation membrane (5), suitable for pervaporation separation of aromatics and oxygenates, such as ethanol, from lower octane aliphatic components in gasoline feed. Examples of suitable membranes may be found in U.S. Pat. No. 8,119,006 and U.S. application Ser. Nos. 13/446,488 and 61/476,988, all of which are hereby incorporated by reference herein for their respective relevant disclosures. The saturated vapor can condense a liquid layer onto the membrane rich in the constituents of the feed that comprise the preferred permeate (10), while passing less desired feed constituents as retentate (9). The term "preferred permeate" means the constituents of the feed that the invention's user wishes to separate, as permeate, from the feed. In the illustrated system, high octane fuel components such as aromatics and ethanol can be a preferred permeate. This stream is shown as the HiRON permeate (11).

The low octane retentate (9) can be combined with the higher boiling separated liquid (6) to obtain the LoRON product (12). In this embodiment, the retentate can contain aliphatic constituents of the feed that have a lower octane than the preferred permeate and can contain substantially lower concentrations of the higher boiling feed components, including additives, found in the feed (1) that can be harmful to the longevity of the membrane.

Referring now to the operation of the pervaporation membrane (5), the saturated vapor feed (7) can contact and can wet the pervaporation membrane (5). A suitable vacuum can be maintained on the permeate side of the membrane to satisfy the flux requirements of the user. Selective sorption and diffusion transport of the molecules of the preferred permeate can serve to separate the preferred species from the remaining feed. The hot permeate vapor can be cooled and condensed on the downstream side of the membrane and collected. An optional educator using the HiRON permeate product as the motive fluid to provide vacuum may be employed for collection of the permeate, as disclosed in U.S. Pat. No. 8,051,828, which is hereby incorporated by reference herein for its relevant disclosure.

The pervaporation membrane (5) can advantageously be a selective membrane, chosen to preferentially permeate the preferred permeate. In a preferred embodiment, where feed (1) comprises gasoline or naphtha, for example, and the preferred permeate is enriched in high octane components, such as aromatic hydrocarbons, pervaporation membrane (5) can be an aromatic selective membrane such as described in U.S. Pat. No. 5,670,052, for example, which is hereby incorporated by reference herein for its relevant disclosure. In another preferred embodiment, where the gasoline feed also contains oxygenates such as ethanol, an aromatic selective ethanol stable membrane could additionally or alternately be used, such as described in U.S. Pat. No. 8,119,006 and/or co-pending U.S. Provisional Application No. 61/476,988, each of which is hereby incorporated by reference herein for its relevant disclosure. The selective pervaporation membrane (5) may include a physical porous support means (not shown) such as alumina, for example, capable of providing physical support of the selective pervaporation membrane under the temperature, pressure, and materials conditions described herein. Alternative supports can include, but are not limited to, sintered metal or ceramic porous media. A preferred support means can include an asymmetric porous media such as a porous ceramic tube or monolith having a microporous surface material, such as described in U.S. Pat. No. 8,119,006 and co-pending U.S. Provisional Application No. 61/476,988, each of which is hereby incorporated by reference herein for its relevant disclosure.

In an alternate embodiment, selective pervaporation membrane (5) can comprise a cross-linked polyimide-polyadipate membrane polymer and/or a cross-linked epoxy amine polyether membrane polymer supported on a porous ceramic support means.

A feature of the present invention can include the substantially adiabatic operation of the pervaporation membrane (5). The pervaporation process can typically be endothermic. As previously described, the feed material can be maintained as partially vaporized. Progressive condensation of the higher boiling temperature constituents of the saturated vapor phase feed onto the pervaporation membrane can supply heat to the membrane, offsetting the heat lost to the endothermic pervaporation process.

Yet another feature of the present invention can include the liquid layer that contacts the separation membrane (5). The membrane temperature $T_f$ and the pressure on the membrane feed side $P_f$ can be maintained to condense a relatively thin layer of preferred permeate rich condensate on the membrane surface. Though not intending to be bound by any particular theory, in a preferred embodiment, the liquid layer can be maintained as a relatively thin layer to facilitate achieving and maintaining both thermal and compositional equilibrium between vapor, liquid and membrane. In the embodiment where feed comprises conventional gasoline or naphtha and where the preferred permeate comprises the high octane aromatic and oxygenate constituents of the feed, the liquid layer can be maintained by control of $T_m$ and $P_f$ such that the condensation rate of aromatic-rich constituents can be roughly proportional to the permeation rate of such constituents. Operating temperatures from about 80° C. to about 180° C. (e.g., from about 120° C. to about 140° C.) and pressures from about 1 barg to about 10 barg (e.g., about 3 barg to about 5 barg) can be preferred.

Permeate (10), having increased concentration of the preferred permeate, can be condensed and collected by conventional means illustrated by HiRON reservoir (11).

Retentate (9) can be collected by conventional means illustrated by LoRON product reservoir (12). Optionally, the separated liquid product stream (6) can be collected and combined with the retentate stream (9) in the LoRON product reservoir (12).

Figure 3:
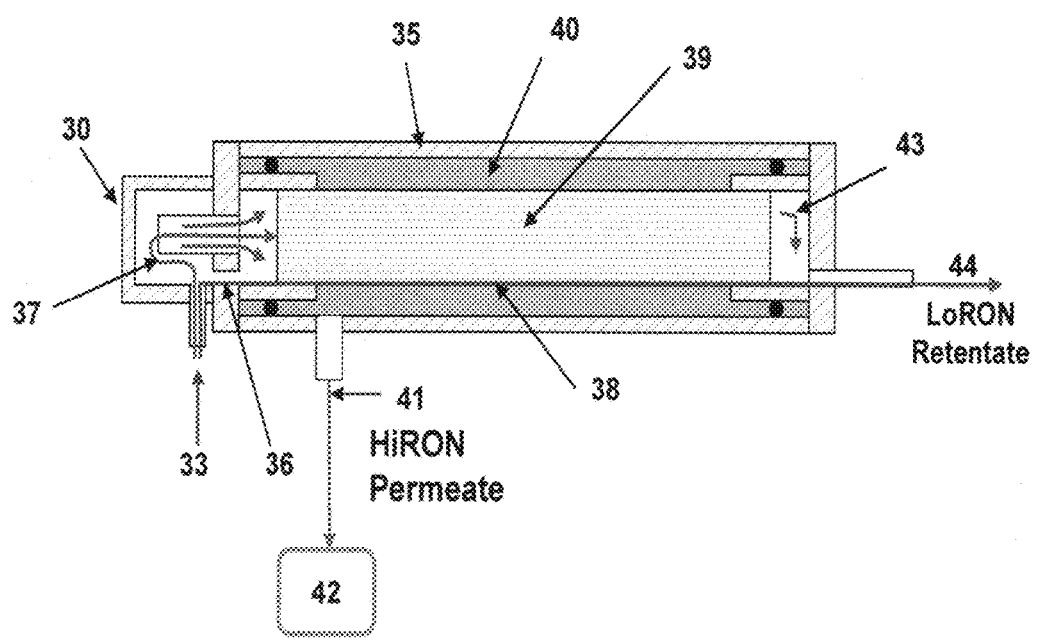
FIG. 3 shows a cross sectioned schematic of the integrated cyclone separation apparatus for improved lifetime membrane separation system, with FIG. 3B showing the internal configuration of the membrane support and bypass channels.

Referring now to FIG. 3, there is shown a cross sectioned view of the improved lifetime separation system of the present invention. In the figure, a mixed liquid/vapor feed (33) can enter cyclone (30), here shown as physically integrated with the membrane system (35), detailed hereinafter. The feed can be separated into a saturated vapor phase and a higher boiling liquid phase. The liquid portion of the feed can be separated and directed to one or more bypass channels, shown as (38) in both FIGS. 3 and 3B. The saturated vapor phase feed (37), separated from the liquid fraction (36), can be directed to the pervaporation membrane (39) for pervaporation separation, which, in the embodiment of a gasoline or naphtha feed, can selectively permeate aromatics, and, when present in the feed, oxygenates such as ethanol over aliphatics, to produce an octane enhanced permeate (41) stored in HiRON reservoir (42). In one embodiment of the invention, the pervaporation membrane can be deposited onto a ceramic substrate having a plurality of generally axial aligned passageways. Passageways (39) can be coated, internally along the walls of the passageway, with the pervaporation membrane. The saturated vapor can be fed axially through the passageways (39), permeating through the membrane radially, into the ceramic, then into the annulus (40), exiting as HiRON permeate at (41), stored in HiRON reservoir (42).

The higher boiling point materials, including feed constituents understood to be deleterious to the longevity of the membrane, can be contained in the liquid portion of the separated feed, here shown as (36), being directed to a membrane bypass means (38) that bypasses the pervaporation membrane, then joining with the retentate of the membrane, here shown as stream (43). The collective streams of the stream exiting the bypass means (38) and the retentate from the pervaporation membrane can be accumulated in the LoRON accumulation means (44), which comprises the lower octane stream, when gasoline or naphtha is the primary feed being separated.

Figure 3B:
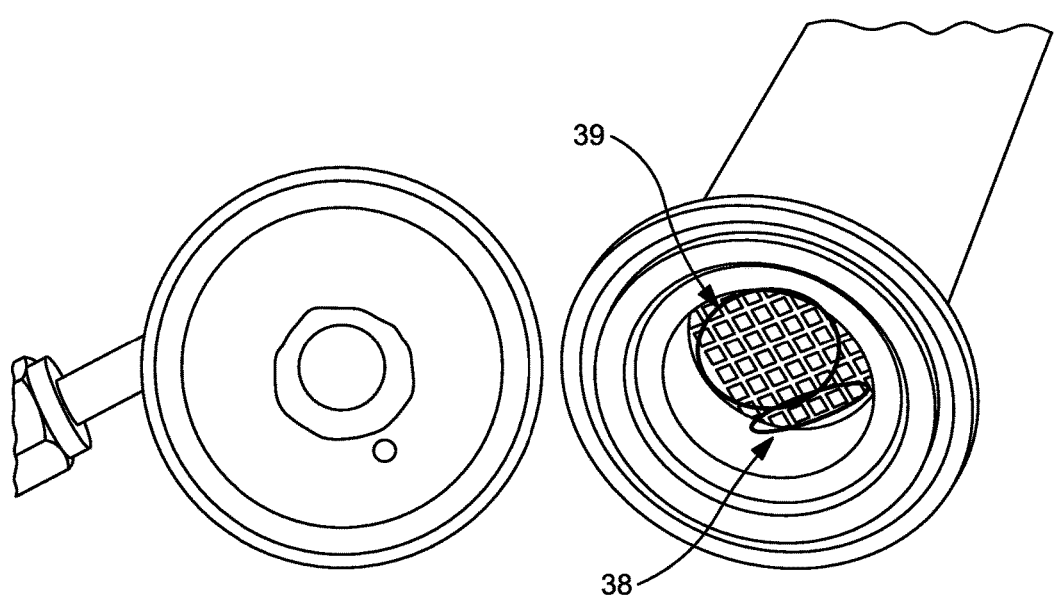

FIG. 3B illustrates an embodiment of the invention where the pervaporation membrane is deposited onto a ceramic monolithic substrate having a plurality of generally axial aligned passageways. Passageways (39) can be coated, internally along the walls of the passageway, with the pervaporation membrane. Bypass passageways (38) can serve as a bypass of the pervaporation membranes for the separated liquid fraction of the feed (36).

The examples presented below illustrate and exemplify the subject matter for this invention.

EXAMPLES

Example 1

A crosslinked-polyether membrane on a ceramic monolith support was prepared by slip-coating a CeraMem® 0.01 micron porosity TiO2/SiC 0.1 m2 monolith test element (CeraMem® Corporation, Newton, Mass.) with a pre-polymer solution made from Jeffamine® D400 (Sigma-Aldrich/Huntsman) and 1,2,7,8-diepoxyoctane (Sigma-Aldrich). 1,2,7,8-diepoxyoctane, referred to herein as DENO.

The D400-DENO polymer precursor solution was prepared at an epoxy/amine hydrogen ratio of 1.05, using 6 wt. % ethanol as catalyst, by reaction at 100° C. in a sealed reaction flask, stirring for 4 hours, followed by quenching and dilution with toluene to a final pre-polymer concentration of 25%. This solution had a viscosity of 2.3 cP at room temperature.

Two coatings were made. The first coating was made by filling the monolith channels with a 25% solution of the D400-DENO pre-polymer solution against a $N_2$ backpressure of about 15 kPag, to limit infiltration of the support by the coating solution, and with ultrasonic vibration for 30 seconds to help ensure removal of entrained gas bubbles. After draining, the channels were filled, vibrated and then drained again. The coated element was dried and then cured for one hour at 150° C. in air. A second coating was made similarly using a 12.5% solution of the polymer precursor in toluene at viscosity of about 1.3 cP. Vacuum was applied after filling the channels, with no change in liquid level prior to draining. The coated element was dried and then cured 12 hours at 150° C. in air. Total polymer weight was 2.12 g. A vacuum test of the cured element indicated good polymer coating integrity, with a pressure increase of only 0.1 kPa/min when isolated against air (in channels) at 18 kPa.

Example 2

The D400-DENO polymer coated ceramic monolith from Example 1 was evaluated using a model feed having the composition 10 wt. % ethanol, 45 wt. % toluene, and 45 wt. % n-Heptane. The monolith was mounted vertically with feed down-flow through a Bete WL1/4-90° nozzle (Bete Fog Nozzles, Inc. Greenfield, Mass.). Pervaporation test conditions were established at 1.0 g/s feed at 600 kPa(abs) pressure and a membrane inlet temperature of 155° C. Vacuum was applied by means of an educator (Fox Valve Development Corp, Dover, N.J.) to obtain a permeate pressure of 12 kPa. These conditions were maintained for nearly 160 hours resulting in a stable permeate rate of 0.077 g/s, corresponding to a yield of 7.7% on feed, with an aromatic selectivity of 3.0 and an aromatic+ethanol selectivity of 3.8. Aromatic selectivity (AS) is here defined as the weight fraction of aromatics (A) in the permeate product relative to the feed (Ap/Af) divided by the aliphatic hydrocarbon (NA) fraction of the permeate product relative to the feed (NAp/NAf). The aromatic+ethanol selectivity (AES) is defined similarly, where the weight fraction of ethanol in the permeate (Ep) and ethanol in the feed (Ef) are included in the calculation:

$$AES=((Ap+Ep)/(Af+Ef))/(Nap/NAf)$$

Example 3

The membrane used in Example 2 was used to separate a gasoline blend containing 10% ethanol, prepared by blending 200 proof ethanol with a commercially available, fully additized summer grade RUL (Regular Unleaded) gasoline. Pervaporation test conditions were established at 0.2 g/s feed at 500 kPa(abs) pressure and a membrane inlet temperature of 155° C. At these conditions, approximately 80% of the gasoline was vaporized, while about 20% remained E10 model feed was 0.054 g/s after 1195 hours continuous testing, including the E10 gasoline test disclosed in Example 3.

After 25 hours with the additized model feed the permeate rate had increased slightly to 0.059 g/s as presented in Table 1. These conditions were maintained for about 140 hours resulting in a stable permeate rate of 0.058 g/s and nearly constant yield on feed of 5.7 wt. %. Permeate rates remained stable after returning to the un-additized E 10 model feed for an additional 65 hours. Compositions of the permeates were all very similar, with substantial concentration of both ethanol and toluene. There was no significant change in aromatic or ethanol+aromatic selectivity in transitioning to or from the additized E10 Model feed. Notably, the all the permeates remained colorless, while the retentates obtained with the additized feed were yellow in color, similar to the dyed feed. This indicates that the dye (Dyeguard Yellow R) did not permeate the membrane.

TABLE 1

E10 Model Feed with Gasoline Additives
Conditions: E10MF 1.0 g/s, 155° C., 600 kPa P-retentate, 12 kPa P-permeate

Figure 4:
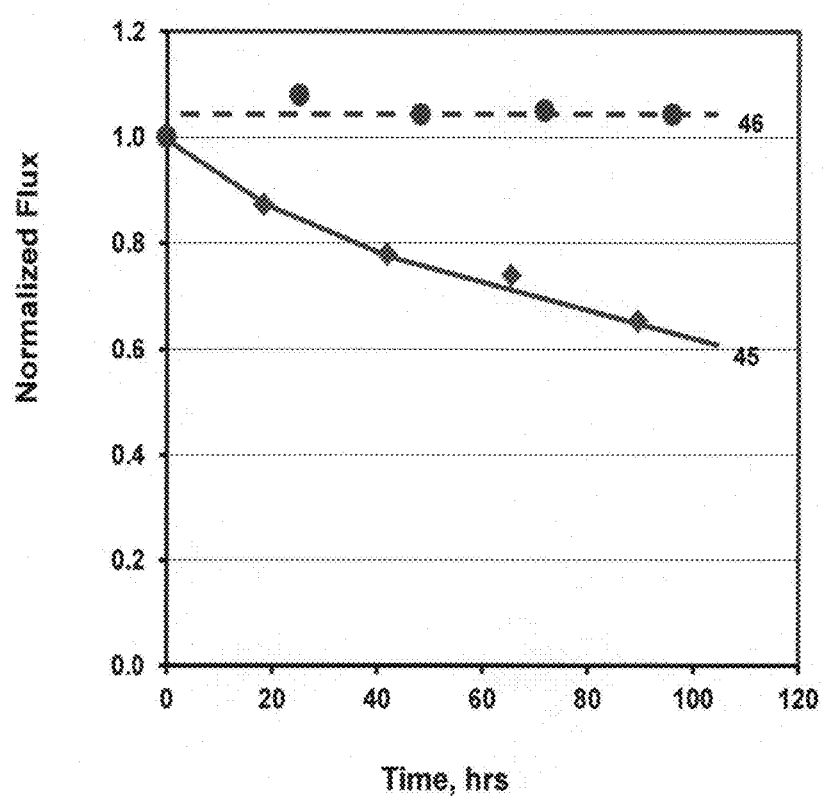
FIG. 4 shows a graph of the decline of flux of a conventional membrane system.

|  | E10 Model Feed | E10 Model Feed with Additives | E10 Model Feed with Additives | E10 Model Feed |
| --- | --- | --- | --- | --- |
| Time on Stream, hours | 1195 | 1220 | 1363 | 1434 |
| Permeate Rate, g/s | 0.054 | 0.059 | 0.058 | 0.059 |
| Yield. Wt % | 5.3 | 5.7 | 5.7 | 5.7 |
| Density, g/cc | 0.8134 | 0.8133 | 0.8133 | 0.8129 |
| Composition, wt % |  |  |  |  |
| Ethanol | 32.9 | 32.5 | 31.9 | 32.8 |
| n-Heptane | 12.8 | 12.9 | 13.3 | 13.1 |
| Toluene | 54.3 | 54.6 | 54.8 | 54.1 |
| Aromatic Selectivity | 4.30 | 4.32 | 4.22 | 4.22 |
| Ethanol + Aromatic Selectivity | 5.70 | 5.68 | 5.54 | 5.57 |
| Color Permeate | Colorless | Colorless | Colorless | Colorless |
| Color Retentate | Colorless | Light Yellow | Light Yellow | Colorless | liquid. The vapor-liquid mixture was distributed across the membrane face by the spray nozzle noted in Example 2. Vacuum was applied by means of an eductor to obtain a permeate pressure of about 25 kPa. These conditions were maintained for about 100 hours. During this time the permeate rate decreased from 0.0234 g/s to 0.0153 g/s. This represents a flux loss of nearly 35%. The normalized data are shown graphically in FIG. 4, trace (45).

Example 4

The model feed described in Example 2, was combined with additive components at concentrations typically used in commercial RUL gasoline. These included metal deactivator (N,N'-Disalicylidene-1,2-propanediamine) at 3.42 ppmw, hindered amine antioxidant (N,N'-Di-2-butyl-1,4-phenylenediamine) at 1.44 ppmw phenolic antioxidant (2,6 di-tert-butylphenol) at 2.4 ppmw and a dye (Dyeguard Yellow R) at 1.45 ppm. No detergent additive was used in this test. Conditions were about the same as used in Example 2. Pervaporation test conditions were established at 1.0 g/s feed at 600 kPa(abs) pressure and a membrane inlet temperature of 155° C. Vacuum was applied by means of an eductor to obtain a permeate pressure of 12 kPa. Prior to switching to the additized model feed, the permeate rate on Normalized permeate flux results are shown graphically in FIG. 4 for the additized E10 model feed. Essentially no additional aging of the membrane occurred when processing the additized model feed, trace (46). Comparing the results obtained with the additized model feed of this example, with those obtained using the E10 gasoline blend from Example 3, shows the loss of flux attributed to running the commercial gasoline, trace (45). Over the same period of time the gasoline showed a flux loss of nearly 35-40%, while the similarly additized model feed showed no loss of flux.

Example 5

The gasoline blend containing 10% ethanol, prepared by blending 200 proof ethanol with a commercially available, fully additized summer grade RUL (Regular Unleaded) gasoline from Example 3 was partially vaporized and separated into two fractions by use of a cyclone separator.

The cyclone separator, comprised a 1" diameter, 0.065" wall thickness, 316 stainless steel tube 3" long; with a tangential inlet tube at the top made from ⅜" diameter, 0.035" wall, tubing flattened to about ⅛" at the interface; a flat cap on top with a ⅜" diameter, 0.035" wall tube coaxial to the outer tube extended ¾" below the tangential inlet; and a ¼" outlet tube exiting at the bottom from a conical reducer. The separator was insulated when in use.

The gasoline feed was partially vaporized at 140° C. and 400 kPaa by passing 1.0 g/s feed through a 2' long by ¼" OD U-tube heated by condensing steam. The vapor/liquid mixture was separated by passing through the cyclone separator. Saturated gasoline vapor exited the top of the cyclone through the coaxial tube. Separated liquid exited the cyclone through the bottom tubing. To help ensure separation, a small amount of vapor was taken with the liquid fraction. The bottoms product was cooled by use of a heat exchanger and the rate controlled by a mass flow controller.

TABLE 2

Cyclone Separation of Partially Vaporized E10 Chiba SRUL Blend

|  | Gasoline Feed | Cyclone Overhead | Cyclone Bottoms |
| --- | --- | --- | --- |
| Temperature, C. | 140 | 138 | 138 |
| Pressure, kPa(abs) | 400 | 400 | 400 |
| Yield. Wt % | 100.0 | 69.3 | 30.7 |
| Density, g/cc | 0.7445 | 0.7290 | 0.7866 |
| Color | Light Red | Colorless | Red |
| Composition, wt % |  |  |  |
| Ethanol | 10.1 | 12.9 | 3.7 |
| C3-C5 HC | 14.7 | 18.6 | 5.9 |
| C6 + NA | 43.3 | 43.5 | 42.8 |
| Aromatics | 32.0 | 25.1 | 47.6 |
| 2-Ring Aromatics | 0.15 | 0.00 | 0.50 |
| 3-Ring + Aromatics | 0.03 | 0.00 | 0.11 |

At these conditions, about 73 to 75 wt. % of the feed was vaporized. The bottoms rate was maintained at 0.3 g/s. The overhead product was condensed by use of a glycol cooled heat exchanger. Several gallons of each product were collected to provide feed for testing.

The cyclone separation conditions, product properties and compositions obtained by gas chromatographic analysis are identified in Table 2. The cyclone overhead product was notably colorless, enriched in ethanol and lower boiling hydrocarbons, and contained essentially no multi-ring aromatics (<5 ppm 2-ring naphthalenes). The cyclone bottoms product was enriched in higher boiling hydrocarbons, with a darker red color than the feed. Nearly all of the multi-ring aromatics, and high boiling additives and dyes remained in the cyclone bottoms product.

Example 6

The cyclone overhead prepared in Example 5 was used as feed to the membrane used in preceding Examples 2-4. Conditions were established similar to those used for the E10 gasoline in Example 3 at 0.2 g/s feed rate, 600 kPa (abs), 157° C., and a permeate pressure of 27 kPa(abs) in order to achieve a nominal yield of 10% permeate. The pressure was increased about 100 kPa to help ensure a vapor-liquid mix at the membrane inlet when using the gasoline overhead as feed. These conditions were maintained for about 210 hours and the permeate rate monitored for aging. During this time period, the permeate rate obtained with the cyclone overhead as feed remained nearly constant, with the yield increasing slightly from 8.8 to 9.0%. The permeate density, 0.784 g/cc, is substantially greater than that of the retentate at 0.731 g/cc consistent with permeation of the higher density aromatic and ethanol components. Both the permeate and retentate were colorless, consistent with the colorless feed.

The cyclone bottoms prepared in Example 5 was used as feed to the membrane used in the preceding examples. A 0.2 g/s feed rate, 500 kPa (abs), 166° C., and a permeate pressure of 27 kPa(abs) were established. The temperature was increased by about 10° C. in order to achieve a nominal initial yield of 10% permeate. These conditions were maintained for about 150 hours and the permeate rate monitored for aging. During this time period, the permeate rate obtained with the cyclone bottoms as feed declined substantially, with the yield decreasing from 7.8 to 3.3%. The permeate density, 0.811 g/cc, is substantially greater than that of the retentate at 0.762 g/cc, consistent with permeation of the higher density aromatic components. The permeate was colorless, but the retentate was a dark red color consistent with the red bottoms feed dye concentration.

Figure 5:
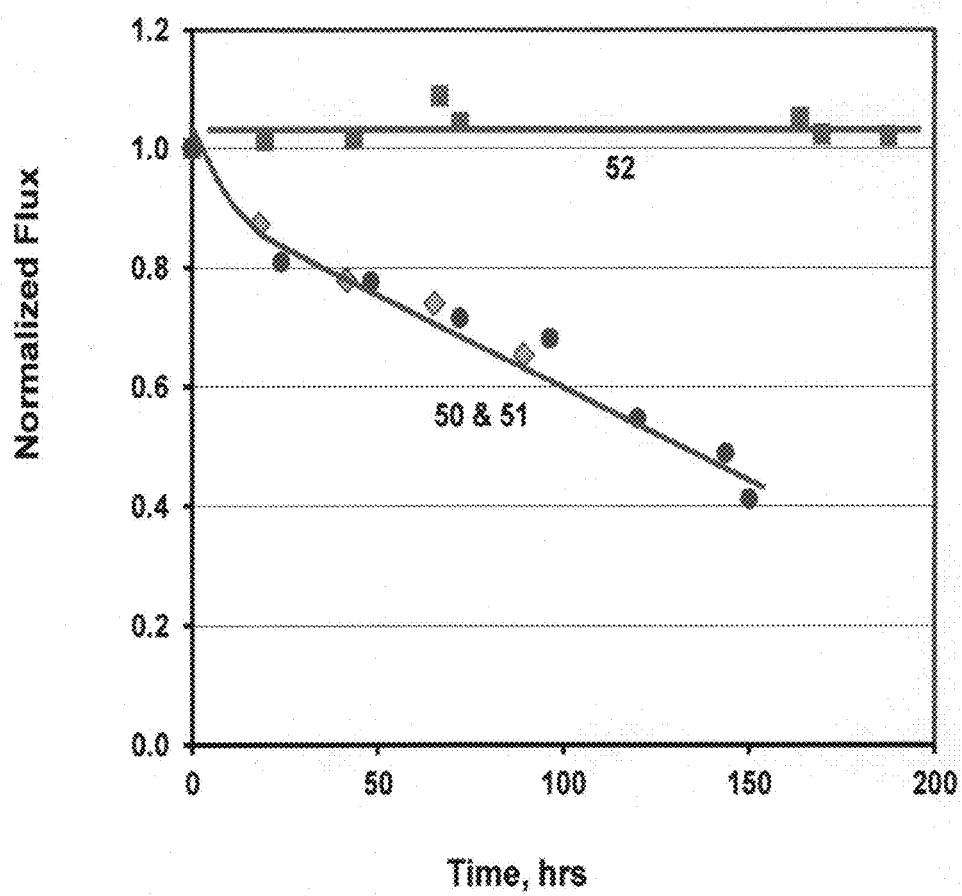
FIG. 5 shows the performance of the improved membrane lifetime system contrasted to a conventional membrane system.

A comparison of the normalized permeate flux is shown in FIG. 5. The flux decline of the gasoline (50) and gasoline bottoms (51) as feed are similar, both losing about 40% flux during first 100 hours on feed. The results for the gasoline overhead, trace (52), as feed showed no substantial change in flux over the time period and beyond. The results indicate that the higher boiling components of the gasoline feed are primarily responsible for flux decline.

Example 7

A crosslinked-polyether membrane on ceramic monolith support was prepared by slip-coating a Corning® 0.01 micron porosity TiO2/Mullite 0.21 m2 monolith test element, with nominally 1 mm round channels, (Corning® Inc., Corning, N.Y.; 1L1R-1045) with a DENO-D400 pre-polymer solution as described in Example 1. A total of four coatings using 12.5% pre-polymer solution and a final 3.7% coating gave a final polymer weight of 2.17 g after curing.

The overhead outlet of the cyclone separator described in Example 5 was connected directly to the inlet nozzle of the membrane monolith. The monolith was mounted vertically down-flow as in Example 2. The bottoms from the cyclone was directed through a site tube, heat exchanger cooler and mass flow controller. Permeate, Retentate and Bottoms products were collected separately after cooling.

A gasoline blend containing ethanol, was prepared by blending 200 proof ethanol with a commercially available, fully additized 90 RON winter grade RUL (Regular Unleaded) gasoline.

Conditions comprising 0.5 g/s feed and 500 kPa(abs) inlet pressure with a Cyclone inlet temperature of about 160° C. were established. About 90% of the gasoline was vaporized, while 10% remains liquid. Overhead saturated vapor from the cyclone at about 0.45 g/s was cooled slightly prior to the membrane inlet to about 152° C. to ensure a small fraction of liquid present at the inlet nozzle.

Pervaporation conditions for the membrane were an inlet temperature of about 152° C. an outlet control pressure of about 500-510 kPa(abs) and permeate pressure of about 35 kPa. Typical retentate temperatures of about 143° C. and permeate temperatures of about 106° C. were observed. Both the permeate and retentate were colorless, while the bottoms product was red, indicating no carryover of dye in the overhead feed to the membrane.

Figure 6:
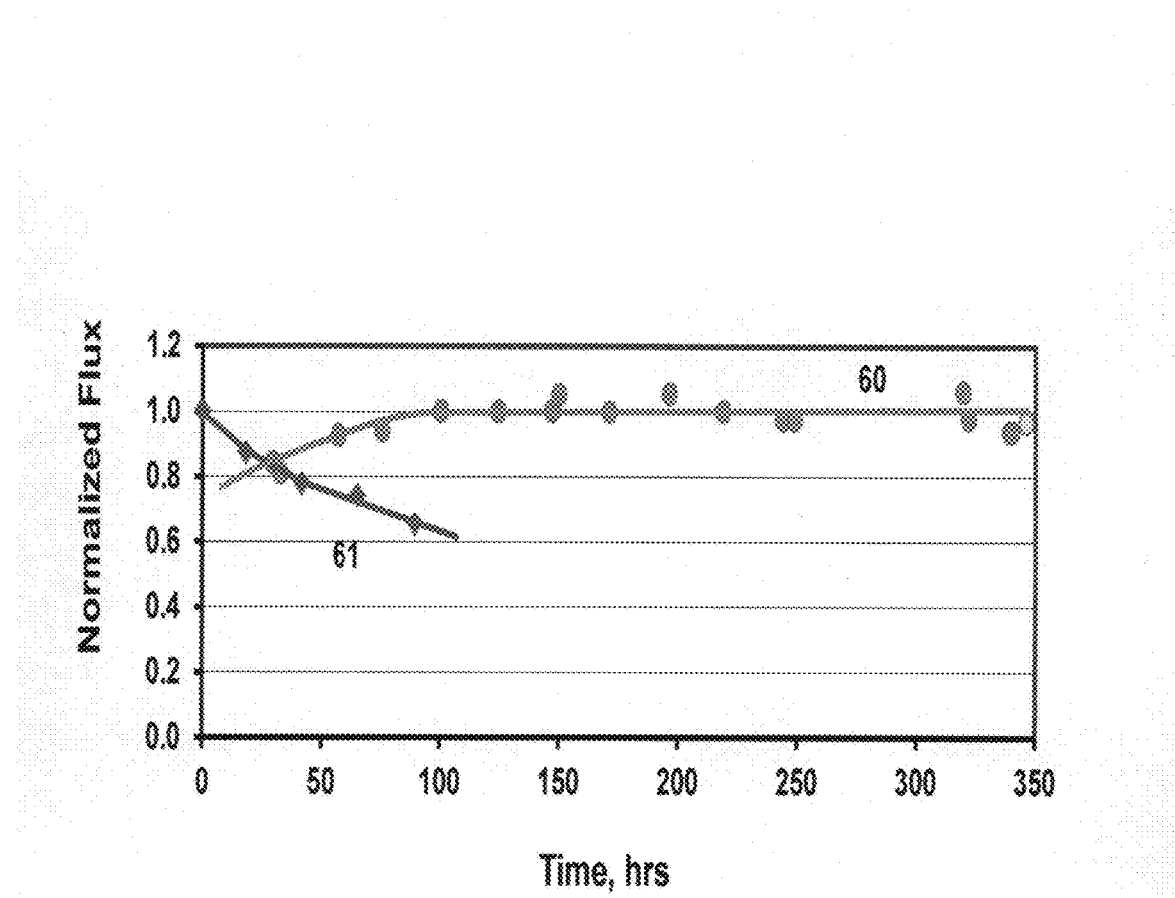
FIG. 6 shows the performance of a fully integrated cyclone separator with a horizontal monolith having an integrated cyclone.

FIG. 6 shows the aging performance of the membrane with the integrated cyclone. Unlike previous results obtained with E10 gasoline feed, the integrated cyclone membrane combination actually showed an increase in flux, trace (60) during the first 100 hours of operation with permeate yield improving from 17.5% to 20.8%. This 20% increase in flux is a substantial improvement when compared to the 40% loss of flux in the same timeframe with E10 gasoline run without the cyclone, trace (61). The permeate yield remained about constant for an additional 220 hours of testing.

Table 3 provides an analysis of the products at 21.6% yield on total feed after 150 hours on stream revealed that the permeate RON of about 100.8 was substantially improved compared with the retentate RON of 92.0. The Bottoms product had an intermediate RON of about 94.5. The ethanol content of the feed blend used in this study was lower than typical E10. Both ethanol and aromatics were concentrated in the permeate, while the retentate showed an increase in light hydrocarbons and C5+ non-aromatics.

TABLE 3

Integrated Cyclone and Bottoms External Bypass

|  | Feed | Permeate | Retentate | Bottoms |
|---|---|---|---|---|
| Yield. Wt % | 100.0 | 21.6 | 67.6 | 10.8 |
| Density, g/cc | 0.7445 | 0.7807 | 0.7133 | 0.7525 |
| Color | Light Red | Colorless | Colorless | Med Red |
| Octane, RON D2699 | 94 | 100.8 | 92.0 | 94.5 |
| Composition, wt % |  |  |  |  |
| Ethanol | 5.5 | 11.8 | 4.1 | 3.5 |
| C3-C5 HC | 12.4 | 6.0 | 12.0 | 7.8 |
| C6 + NA | 42.1 | 23.4 | 50.0 | 39.3 |
| Aromatics | 40.1 | 58.8 | 33.9 | 49.4 |

Example 8

This example integrated the cyclone separator directly into the inlet to the membrane as illustrated in FIGS. 3 and 3B. A 0.13 m2, 0.01 micron porosity Corning monolith, with 92 nominally 1.5 mm round channels, coated with 1.06 g of a DENO-D400 polymer membrane. The E10 gasoline feed flowing at 0.5 g/s was preheated to 160° C. at 500 kPa(abs). This vaporized about 90% of the feed, similar to Example 7. The partially vaporized feed was directed to the inlet of the fully integrated cyclone configured for horizontal operation. No insulation was used. A thermocouple located on the centerline within the vapor stream to the monolith indicated about 152° C. inlet temperature, corresponding to a final vapor fraction of about 80%. Corresponding retentate outlet was 138° C., and permeate outlet 108° C. Permeate pressure was 31 kPa. The liquid bottoms fraction of the gasoline was directed to a limited number of the monolith membrane channels. Membrane channels used in this manner would be expected to age more rapidly than those used to process the vapor fraction. The remaining channels were contacted with the saturated vapor fraction. When mounted horizontally, the liquid fraction is directed to the lower channels. The bottoms liquid retentate combines with the retentate from the channels that process the saturated vapor portion of the feed. This combined product typically has a lower octane rating (RON) than the gasoline feed. Permeate from all of the feed processed is combined by the commonality of the porous monolith structure and typically has a higher octane rating than the feed.

During the first 50 hours on stream the permeate yield increased from an initial yield of about 20% to a maximum of nearly 27% yield and a RON of 101. The permeate yield decreased to 18% at 250 hours, while maintaining a RON of 101. The results are a significant improvement over those obtained with the gasoline vapor-liquid mix introduced as a vapor/liquid spray as in Example 3.

Table 4 provides an analysis of the products at 19.6% yield on total feed after 210 hours on stream. The permeate RON of 101.2 was substantially improved compared with the composite retentate RON of 92.5. Both ethanol and aromatics were concentrated in the permeate, while the retentate showed an increase in aliphatic light hydrocarbons and C5+ non-aromatics. The permeate product was colorless, while the composite retentate product had a slightly more red color than the feed.

TABLE 4

Fully Integrated Cyclone Inlet with Horizontal Membrane Monolith
0.52 g/s, 510 kPa(abs), 155.5° C., 26.7 kPa
P-permeate @ 210 hours on stream

|  | Feed | Permeate | Retentate |
|---|---|---|---|
| Yield. Wt % | 100.0 | 19.6 | 80.4 |
| Density, g/cc | 0.7280 | 0.7845 | 0.7171 |
| Color | Light Red | Colorless | Light Red |
| Octane, RON D2699 | 94 | 101.2 | 92.5 |
| Composition, wt % |  |  |  |
| Ethanol | 7.7 | 11.7 | 6.7 |
| C3-C5 HC | 21.4 | 8.4 | 24.5 |
| C6 + NA | 40.1 | 39.5 | 40.3 |
| Aromatics | 30.8 | 40.3 | 28.5 |

Inspection of the used membrane monolith indicated that the lower channels of the monolith were much darker in color than the upper channels, consistent with limited contacting by the colored cyclone liquid fraction.

In an alternate embodiment, the separated liquid fraction would be directed to monolith channels by means of a conduit from the separator to seal at the monolith face thereby preventing re-mixing with the vapor fraction, and directed to bypass channels such that the separated liquid mostly passes through that portion of the system.

In another embodiment, a portion of the condensed permeate is recycled to the membrane vapor inlet to be used to partially cool the saturated vapor fraction, creating a vapor/liquid mist so that liquid would be present at the monolith inlet, thereby further improving membrane performance. Recycle of permeate also leads to a higher octane permeate product.

What is claimed is:

1. A process for extending the life of a pervaporation membrane for separating high octane components from a gasoline feed stream, including aromatics and non-aromatics and having a boiling point of at least 50° C. comprising:
   heating the gasoline at a temperature $T_f$ under pressure $P_f$ to partially vaporize the gasoline to produce a saturated vapor and a liquid from the gasoline;
   separating the vapor from the liquid;
   directing the vapor to a pervaporation membrane suitable for separating high octane components from a gasoline feed, and collecting the permeate there from in a first retention means;
   directing the liquid and the retentate from the pervaporation membrane to a second retention means.

2. The process of claim 1, wherein said process is carried out adiabatically.

3. The process of claim 2, wherein heat is provided by condensation of the vapor phase.

4. The process of claim 1, wherein said feed stream is a gasoline containing oxygenates that comprise at least one of methanol, ethanol, propanol, and butanol.

5. The process of claim 1, wherein the membrane is a polyester imide copolymer membrane, polyurethane imide membrane, polyimide aliphatic polyester copolymer membrane, diepoxyoctane cross linked/esterified polyimide/polyadiapate copolymer membrane, a cross-linked polyether amine-epoxy membrane, a crosslinked polyether epoxy polymer comprising an aliphatic substituted epoxide and polyetheramine having an Mn from about 230 to about 4000, or a combination thereof.

6. The process of claim 5, wherein the polymer or copolymer membrane is supported by a porous substrate.

7. The process of claim 6, wherein the substrate is a porous ceramic.

8. The process of claim 6, wherein said substrate comprises a porous ceramic monolith, and wherein said membrane is a crosslinked polyimide-polyadipate polymer, coating at least a portion of the ceramic.

9. The process of claim 6, wherein said substrate comprises a porous ceramic monolith, and wherein said membrane is a crosslinked polyether epoxy polymer comprising an 1,2,7,8 diepoxy-n-octane and poly(propylene glycol) bis(2-aminopropyl ether)s having an Mn of about 400, coating at least a portion of the ceramic.

* * * * *